US009399756B2

(12) United States Patent
Gao et al.

(10) Patent No.: US 9,399,756 B2
(45) Date of Patent: Jul. 26, 2016

(54) FUNCTIONALIZED FULLERENES AS A BIOMASS STIMULANT AND A LIFE EXTENSION AGENT

(75) Inventors: Jie Gao, Oak Ridge, TN (US); Vijay Krishna, Gainesville, FL (US); Wei Bai, Gainesville, FL (US); Benjamin L. Koopman, Gainesville, FL (US); Brij M. Moudgil, Gainesville, FL (US); Paul Anthony Indeglia, Amhurst, NH (US); Kevin Michael Folta, Gainesville, FL (US); Angelina Tsenova Georgieva, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 131 days.

(21) Appl. No.: 13/638,054

(22) PCT Filed: Apr. 7, 2011

(86) PCT No.: PCT/US2011/031581
§ 371 (c)(1),
(2), (4) Date: Sep. 28, 2012

(87) PCT Pub. No.: WO2011/127285
PCT Pub. Date: Oct. 13, 2011

(65) Prior Publication Data
US 2013/0035398 A1    Feb. 7, 2013

Related U.S. Application Data

(60) Provisional application No. 61/322,031, filed on Apr. 8, 2010.

(51) Int. Cl.
| | | |
|---|---|---|
| A01N 31/08 | (2006.01) | |
| A61K 31/05 | (2006.01) | |
| C12N 1/38 | (2006.01) | |
| C12N 1/12 | (2006.01) | |
| C12N 1/14 | (2006.01) | |
| B82Y 5/00 | (2011.01) | |

(52) U.S. Cl.
CPC .. *C12N 1/38* (2013.01); *C12N 1/12* (2013.01); *C12N 1/14* (2013.01); *B82Y 5/00* (2013.01)

(58) Field of Classification Search
None
See application file for complete search history.

(56) References Cited

U.S. PATENT DOCUMENTS

| | | |
|---|---|---|
| 5,994,410 A | 11/1999 | Chiang et al. |
| 2008/0213324 A1 | 9/2008 | Zhou et al. |
| 2009/0076115 A1* | 3/2009 | Wharton et al. ............... 514/410 |

FOREIGN PATENT DOCUMENTS

| | | |
|---|---|---|
| EP | 1894973 A1 | 3/2008 |
| WO | WO 2009-114089 A2 | 9/2009 |

OTHER PUBLICATIONS

Liu et al. ("Liu"), "Adsorption of Dodecahydroxylated-Fullerene Monolayers at the Air-Water Interface," Physica B 283 (2000) 49-52.*
Bosi et al., "Fullerene Derivatives: An Attractive Tool for Biological Applications," European Journal of Medicinal Chemistry, 38 (2003); 913-923.*
Huang et al., "Action of Fullerenols Alleviating Damage of Anthracene on Marine Platymonas Subcordiformis," Marine Science, vol. 28, issue 9, 2004, (Chinese to English Translation).*
Debiane et al., "In vitro Evaluation of the Oxidative Stress and Genotoxic Potentials of Anthracene on Mycorrhizal Chicory Roots," Environmental and Experimental Botany, 64(2008)120-127.*
Chen et al., "Toxicity Assessment of Polycyclic Aromatic Hydrocarbons Using an Air-Tight Algal Toxicity Test," Water Sci Technol., 2006;54(11-12):309-315 (abstract).*
Bogdanovic, G. et al., "Modulating activity of fullerol $C_{60}(OH)_{22}$ on doxorubicin-induced cytotoxicity," *Toxicology in Vitro*, 2004, pp. 629-637, vol. 18.
Chen, Y-W. et al., "Fullerene derivatives protect against oxidative stress in R A W 264.7 cells and ischemia-reperfused lungs," *Am. J. Physiol. Regul. Integr. Comp. Physiol.*, 2004, pp. R21-R26, vol. 287, No. 1.
Chiang, L.Y. et al., "Multi-hydroxy Additions onto $C_{60}$ Fullerene Molecules," *J. Chem. Soc. Chem. Commun.*, 1992, pp. 1791-1793.
Gao, J. et al., Dispersion and Toxicity of Selected Manufactured Nanomaterials in Natural River Water Samples: Effects of Water Chemical Composition, *Environ. Sci. Technol.*, 2009, pp. 3322-3328, vol. 43, No. 9.
Injac, R. et al., "Protective effects of fullerenol $C_{60}(OH)_{24}$ against doxorubicin-induced cardiotoxicity and hepatotoxicity in rats with colorectal cancer," *Biomaterials*, 2009, pp. 1184-1196, vol. 30, No. 6.
Kamat, J.P., et al., "Reactive oxygen species mediated membrane damage induced by fullerene derivatives and its possible biological implications," *Toxicology*, 2000, pp. 55-61, vol. 155, Nos. 1-3.
Lyon, D.Y. et al., "Implications and potential applications of bactericidal fullerene water suspensions: effect of $nC_{60}$ concentration, exposure conditions and shelf life," *Water Science & Technology*, 2008, pp. 1533-1538, vol. 57, No. 10.
Quick, K.L. et al., "A carboxyfullerene SOD mimetic improves cognition and exends the lifespan of mice," *Neurobiology of Aging*, 2008, pp. 117-128, vol. 29, No. 1.
Roberts, J.E. et al., "Phototoxicity and cytotoxicity of fullerol in human lens epithelial cells," *Toxicology and Applied Pharmacology*, 2008, pp. 49-58, vol. 228, No. 1.

(Continued)

Primary Examiner — Jared D Barsky
(74) Attorney, Agent, or Firm — Saliwanchik, Lloyd & Eisenschenk

(57) ABSTRACT

Methods of stimulating an increase in biomass by stimulating the growth, lifespan and/or reproduction of organisms such as fungi, algae, plants, and other aquatic organisms are provided by applying an effective amount of functionalized fullerenes. For example, polyhydroxy fullerenes are effective at low levels of promoting the increase in biomass.

3 Claims, 7 Drawing Sheets

(56) References Cited

OTHER PUBLICATIONS

Wielgus, A.R. et al., "Phototoxicity and cytotoxicity of fullernol in human retinal pigment epithelial cells," *Toxicology and Applied Pharmacology*, 2010, pp. 79-90, vol. 242, No. 1.

Yamawaki, H. et al., "Cytotoxicity of water-soluble fullerene in vascular endothelial cells," *Am. J. Physiol. Cell Physiol.*, 2006, pp. C1495-C1502, vol. 290, No. 6.

Zhou, Z. et al., "Fullerene nanomaterials potentiate hair growth," *Nanomedicine: Nanotechnology, Biology, and Medicine*, 2009, pp. 202-207, vol. 5, No. 2.

Zhu, J. et al., "Tumor-Inhibitory Effect and Immunomodulatory Activity of Fullerol $C_{60}(OH)_x$," *Small*, 2008, pp. 1168-1175, vol. 4, No. 8.

* cited by examiner

FUNCTIONALIZED FULLERENES AS A BIOMASS STIMULANT AND A LIFE EXTENSION AGENT

CROSS-REFERENCE TO RELATED APPLICATIONS

This application is the U.S. national stage application or International Application No. PCT/US2011/031581, filed Apr. 7, 2011, which claims the benefit of U.S. Provisional Application Ser. No. 61/322,031, filed Apr. 8, 2010, the disclosures of which are hereby incorporated by reference in their entireties including any figures, tables, or drawings.

BACKGROUND OF THE INVENTION

Since their discovery in 1985, fullerenes ($C_{60}$ or buckyballs) have been among the most widely studied and used carbon-based nanomaterials due to their unique structural and electronic properties that enable numerous industrial, electrical and medical applications. However, the low solubility of these carbon-based nanomaterials in aqueous solutions restricts their use in this medium, stimulating research directed to their dispersion in aqueous solutions. For example, the water solubility of fullerenes can be improved by coupling the fullerene cage with hydrophilic molecules, forming functionalized fullerenes. One example of functionalized fullerenes is polyhydroxy fullerenes (PHFs, also named fullerols or fullerenols) wherein the fullerenes are functionalized with 1 to 48 hydroxyl groups per molecule.

One advantage of functionalized fullerenes is that they reduce oxidative stress by scavenging reactive oxygen species (Chen et al., Fullerene Derivatives Protect Against Oxidative Stress in RAW 264.7 Cells and Iischemia-Reperfused Lungs, *Am. J. Physiol. Regul. Integr. Comp. Physiol.*, 2004, 287(1), R21-R26; Injac et al., Protective Effects of Fullerenol $C_{60}(OH)_{24}$ Against Doxorubicin-Induced Cardiotoxicity and Hepatotoxicity in Rats with Colorectal Cancer, *Biomaterials*, 2009, 30(6), 1184-1196) and have been examined for their antioxidant applications. Furthermore, fullerenes have been disclosed as therapeutics (Chiang et al., U.S. Pat. No. 5,994,410) and for use in cosmetics (Takada et al., European Patent Application Publication No. EP1894973). Some studies indicate that e,e,e-$C_{60}(C(CO_2H)_2)_3$ may extend the lifespan of mice (Quick et al., A Carboxyfullerene SOD Mimetic Improves Cognition and Extends the Lifespan of Mice, *Neurobiology of Aging*, 2008, 29(1), 117-128) and injected amphiphilic fullerenes (($H_{23}C_{11}CO_2)_2CC_{60}C(CO_2CH_2CO_2H)_2$) may stimulate hair growth in mice (Zhou et al., Fullerene Nanomaterials Potentiate Hair Growth, *Nanomed. Nanotechnol. Biol. Med.*, 2009, 5(2), 202-207; Zhou et al., U.S. Patent Application Publication 2008/0213324 and Keply et al., WO/2009/114089). However, no reproductive effect of functionalized fullerenes has been observed so far.

As the global production of fullerenes and their derivatives is rapidly growing, fullerene containing products will inevitably enter various environments during their production, use and disposal. Among these environments, aquatic systems are probably the primary sink for carbon-based nanomaterials (Lyon et al., Implications and Potential Applications of Bactericidal Fullerene Water Suspensions: Effect of $NC_{60}$ Concentration, Exposure Conditions and Shelf Life, *Water Sci. & Technol.*, 2008, 57(10), 1533-1538; Gao et al. Dispersion and Toxicity of Selected Manufactured Nanomaterials in Natural River Water Samples: Effects of Water Chemical Composition, *Environ. Sci. & Technol.*, 2009, 43(9), 3322-3328). Therefore, it is critical to identify the potential impact of this nanomaterial in an ecological system and, where possible, to positively exploit their introduction into a controlled environment.

BRIEF SUMMARY

Embodiments of the invention are directed to providing effective dosages of functionalized fullerenes, where an exposed organism exhibits enhanced biomass productivity.

An embodiment of the invention is directed to a method of stimulating growth and/or reproduction in an organism comprising administering an effective amount of functionalized fullerenes to effect a more rapid growth of biomass. The organism can be selected from fungi, plant or animal kingdom. The functionalized fullerenes are fullerenes ($C_x$ where x is 20 to 1500) with side groups attached to the fullerene by covalent bonds, ionic bonds, Dewar coordination, Kubas interactions, or any combination thereof. Useful side groups include, but are not restricted to, OH, Br, H, Gd, Ti, and $C(COOH)_2$ groups.

One embodiment of the invention is directed to a method of expanding the lifespan of a living organism comprising administering an effective amount of functionalized fullerenes.

DETAILED DISCLOSURE

Fullerenes and their derivatives have caused substantial concerns due to their reported environmental and toxicological effects. Surprisingly, the inventors have discovered that at appropriate levels, functionalized fullerenes could induce significant stimulation of growth and reproduction and extend lifespan in a variety of organisms, including fungi, plants, algae, and other aquatic organisms.

For the purpose of this invention, the term "fullerenes" is used to define a general class of molecules that exists essentially in the shape of a three dimensional polyhedron containing from 20 to 1500 carbon atoms, and which comprises carbon atoms as the predominant element from which they are composed. The fullerenes include but are not limited to C-28, C-32, C-44, C-50, C-58, C-60, C-70, C-84, C-94, C-250 and C-540. (According to this nomenclature, the fullerene which contains 60 carbon atoms is denoted C-60, the fullerene which contains 70 carbon atoms is denoted C-70, etc.) Functionalized fullerenes refer to fullerenes (C), where x is 20 to 1500) with side groups attached to the outer surface of the cage via covalent bonds, ionic bonds, or Dewar coordination, or Kubas interactions, or any combination thereof. The side groups can be either inorganic, including, but not exclusive to, OH, Br, H, Gd, Ti, organic, including, but not exclusive to, $C(COOH)_2$, or any combination of organic and/or inorganic functional groups. The number of functional groups attached per cage of fullerene can vary from 1 to a majority of the number of carbons in the fullerene cage. Functionalized fullerenes have different physical and chemical properties based on the type and number of side groups. The functionalized fullerenes, which are formally molecules, have dimensions that are in excess of a nanometer in diameter and as such constitute nanoparticles.

Figure 1:
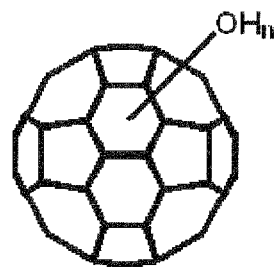
FIG. 1 shows structures of polyhydroxy fullerenes (PHFs) ($C_{60}(OH)_n$, n=1-48) that can be employed in embodiments of the invention.

In one embodiment, the functionalized fullerenes are polyhydroxy fullerenes (PHFs), for example formula $C_{60}(OH)_n$ shown in FIG. 1, which were first reported by Chiang, L. et. al., *J. Chem Soc, Chem. Commun.* 1992, 1791. PHFs are also referred to as fullerols or fullerenols. The number, n, of —OH groups per fullerene is typically between 1 and 48.

Functionalized fullerenes, such as PHFs, can be used for generation of a biomass source for biofuel production according to an embodiment of the invention. Large quantities of biomass can be promoted by the introduction of a small quantity of PHFs to the site of biomass production. In another embodiment of the invention, functionalized fullerenes can be used in aquaculture to increase the rate of reproduction of aquatic animals, such as fish, oysters, conches and shrimp. In a further embodiment, functionalized fullerenes can be used to promote the growth of fungi, for instance, of the species within the *penicillium* genus which provide antibiotics.

"An effective amount" as used herein refers to a dosage of PHF capable of increasing the biomass; stimulating the growth and/or reproduction of organisms; increasing a population; and/or extending the lifespan of organisms. The effective amount of functionalized fullerenes will vary, depending upon factors including, but not limited to, the target organism species, the type of culture medium, presence or absence of other active ingredients, the method of formulation, the route of delivery, and the fullerene species and properties. The effective amount of functionalized fullerenes is organism dependent, and can be readily determined by one having ordinary skill in the art. For example, in embodiments of the invention, the effective amount of PHFs on green algae can be 0.001 to 5 mg PHF/L, 0.01 to 5 mg/L, and 1 to 5 mg/L. In an embodiment of the invention, the quantity of PHF per cell of algae can be about $1 \times 10^{10}$ to about $3 \times 10^{11}$ molecules/cell. However, it should be understood that functionalized fullerenes, including PHF, under certain conditions may also induce unfavorable responses in the organisms as acknowledged in the prior art (Kamat et al., Reactive Oxygen Species Mediated Membrane Damage Induced by Fullerene Derivatives and Its Possible Biological Implications, *Toxicology*, 2000, 155(1-3), 55-61; Yamawaki et al., Cytotoxicity of Water-Soluble Fullerene in Vascular Endothelial Cells, *Am. J. Physiol. Cell Physiol.*, 2006, 290(6), C1495-C1502; Roberts et al., Phototoxicity and Cytotoxicity of Fullerol in Human Lens Epithelial Cells. *Toxicol. App. Pharmacol.*, 2008, 228 (1), 49-58; Wielgus et al., Phototoxicity and Cytotoxicity of Fullerol in Human Retinal Pigment Epithelial Cells. *Toxicol. App. Pharmacol.*, 2010, 242(1), 79-90).

The functionalized fullerenes of the subject invention can be applied to the organisms as unformulated particles or solutions or as a formulated liquid or solid composition, slurry of particles, or emulsion. In one embodiment of the invention, functionalized fullerenes are added directly to a culture medium. In another embodiment of the invention, a fullerene dispersion or solution is added to the culture. When the functionalized fullerenes are formulated, the composition can optionally include beneficial ingredients and/or inert or inactive ingredient. A "beneficial ingredient" as used herein refers to a substance that is useful or productive, for example, useful for controlling a disease, a pest (including for example an insect, a parasite, a virus, a fungus, and a bacterium), a weed, and/or other contaminates. Beneficial ingredients include but are not limited to pesticides, herbicides, fungicides, fertilizers, and bio-control agents. An "inert or inactive ingredient" as used herein refers to a substance that aids in the operation, for example handling or dispersion to improve the effectiveness of a formulation or composition but is not directly an active ingredient. Inert or inactive ingredients include but are not limited to a carrier, an adherent, a dispersant, a surfactant, a liquid dilutant, a binder, a filler agent, a solvent, a wetting agent, a sticker, an emulsifier, a nutrient, a surfactant, a penetrant, a foaming agent, a solubilizer, a spreader, and a buffer agent.

The following are non-limiting examples, which illustrate procedures for practicing the invention.

Materials and Methods

Preparation of PHF Solution

PHF used in this study was purchased from Nano-C (Westwood, Mass.). A stock solution containing 1000 mg/L of PHF was prepared by dissolving 10 mg of PHF in 10 mL of Nanopure® water and the resultant solution had a characteristic dark brown hue.

96-hour *Pseudokirchneriella Subcapitata* Growth Assay

The culture medium was prepared from stock solutions according to an EPA standard method for preliminary algal assay procedure, which includes three groups of salts: major salts, trace salts and micro salts. The pH of the culture medium was adjusted to 7.5±0.1 with 0.1N NaOH or 0.1N HCl and then filtered through a 0.45 μm membrane and sterilized by autoclaving. A pure culture of *P. subcapitata* was obtained from Hydrosphere Research (Alachua, Fla.) and grown in PAAP medium with EDTA at 25±1° C. A light source (86±8.6 μE $m^{-2}$ $s^{-1}$) and continuous aeration were provided 24 hours per day. New cultures were prepared every week under sterile conditions by transferring approximately 20-30 mL of the mature cultures to 1-2 L of fresh sterile media.

Preliminary experiments involved exposure of the algae to PHF for 96 hours and the population density was determined in a first trial by cell counting with a hemocytometer and in a second trial by absorbance measurements.

Subsequent growth assay was performed in 25 mL Erlenmeyer flasks that were sterilized using an autoclave according to EPA protocol. All samples (i.e. culture media spiked with increasing concentrations of PHF from 0.001 to 20 mg/L) and negative controls were run in triplicates and inoculated with 1 mL of 4 to 7 day old algal cultures. All flasks were placed under the fluorescent lights under identical conditions. The algal growth after 96 hours was determined by cell number count between 3.4 and 8 μm using a Coulter Multisizer III (Beckman Coulter, Inc. Brea, Calif., USA).

Survival and Reproduction Assay Using *Ceriodaphnia dubia*

Moderately hard water (MHW) prepared following an EPA standard method was used as culture media these tests. A pure culture of *C. dubia* was also obtained from Hydrosphere Research (Alachua, Fla.) and kept in 1 L beakers containing 500 mL of MHW in a Pervical™ model #E-30 BX environmental chamber at 25° C. with constant aeration. The light period was 16 hours and the dark period was 8 hours. *C. dubia* was fed with concentrated *P. subcapitata* cells and YCT (made from yeast, cereal leaves and trout chow). The *Daphnia* were fed every other day with 6.67 mL YCT and 6.67 mL algae solution/L culture. The culture medium was changed every other day. Neonates of less than 24 hours were separated from adults daily and used for testing.

The survival and reproduction assays were performed according to an EPA protocol. MHW served as a negative control and was used as the diluent to prepare media with varied concentrations of PHF. Neonates less than 24 hours old were separated from adults and fed for two hours prior to the start of a test. For each test, groups of 5 *Daphnia* neonates were transferred into 30 mL plastic cups containing 20 mL of MHW (controls) or MHW plus PHF at a level of 0.0001, 0.001, 0.01, 0.1, 1, 5 or 20 mg/L for 7 days to assess the effects of PHF on their growth, survival and reproduction. The daphnids were cultured in the environmental chamber at 25±1° C. with a photoperiod of 16:8 hours light:dark and fed with 40 μL of YCT and *P. subcapitata* daily per daphnid. The culture media were renewed three times a week. Every day the survival and number of newborns were recorded and the offspring's produced were separated from the test containers. All sample dilutions and negative controls were run in four replicates and each treatment had a total of 20 daphnids.

Growth Effects of PHF on *C. Dubia*

At each PHF concentration, two neonates were kept in separate cups under identical conditions as other test daphnia and subjected to optical microscopy every day about 1 hour after feeding. To observe growth of the daphnia, each neonate was placed on a glass slide and partially immobilized by the surface tension of water drop. Micrographs were taken and analyzed for size (i.e. core body length) of exposed *Daphnia* and distribution of PHF in the body.

Effect of PHF on the Lifespan of *C. Dubia*

The same daphnids with and without the exposure to PHF that were used for the survival and reproduction assay were kept and tested to determine their lifespan. The daphnids were cultured and fed in the same manner as described for the survival and reproductive assay above. The culture media were renewed three times a week. Every day the number of survivors and number of newborns were recorded and the offsprings produced were separated daily until the death of all daphnids.

Fungi Growth Experiments

Preliminary experiments were conducted with *Aspergillus niger* as a model fungus. Experiments were conducted in a 96-well plate by following standard micro-dilution protocol with two different growth media: RPMI 1640 with 2% glucose and RPMI 1640 with potato dextrose broth. The protocol involves preparing a series of PHF dilutions in a 96 well plate, inoculating the wells with *A. niger*, and using the absorbance at 600 nm as an indicator of a biomass concentration. Visible light absorbance correlates to biomass to indicate fungal growth or inhibition relative to the absorbance measured from a control without PHF as taught in Schwalbe et al., ed., 2007, Antimicrobial Susceptibility Testing Protocols, CRC Press, Boca Raton, Fla.

Pre-prepared RPMI-1640 was obtained from Mediatech Inc., Manassas Va. Potato dextrose broth was prepared in the laboratory. PHF stock solutions were prepared at the respective culture media at concentration of 2000 mg/L, followed by 10 fold dilution with the respective media to give stock solution concentrations of 200, 20 and 2 mg/L. A serial dilution of the PHF stock solution was carried out in 96 well plates. Each plate comprised 12 columns and 8 rows. Each cell was identified by its row letter (A-H) and column number (1-12). Thus, the top, left most well would be cell A1, and the bottom, right most cell would be cell H12. After dilution, inoculation of *A. niger* was carried out following the standard protocol described in Schwalbe et al. The plates were covered with aluminum foil, kept in an orbital shaker with temperature at 37° C. and 75 RPM. Absorbance was measured at 0, 24, 48 hours, using a microplate reader.

PHF contributes to the absorbance in visible light spectrum, interfering with the accuracy of measurement. Thus, a blank containing PHF alone was set up in order that the absorbance induced by PHF itself can be eliminated. The blanks were not inoculated. Incubation and absorbance measurement followed the same procedure as described above.

The equation used for calculating growth or inhibition at a given time is expressed as:

$$\text{Inhibition \%} = \frac{[A_{fungi+PHF} - A_{PHF(blank)}] - [A_{control} - A_{control(blank)}]}{[A_{control} - A_{control(blank)}]} \times 100\% \quad (1)$$

Where $A_{fungi+PHF}$ is the absorbance of a given concentration of PHF with *A. niger* inoculums, $A_{PHF(blank)}$ is the absorbance of a given concentration of PHF, $A_{control}$ is the absorbance of *A. niger*, and $A_{control(blank)}$ is the absorbance of culture media alone.

Further experiments were conducted on edible substrates such as bread and peaches. PHF and *A. niger* inoculum were deposited on bread and peaches by spraying. Both sides of a slice of bread were sprayed with deionized (DI) water to render it moist. Each spray contained no more than 0.11±0.01 mL of liquid. The spraying protocol is given in Table 1, below. PHF solutions (BuckyUSA) were prepared in sterile deionized water with concentrations ranging from 0.1 to 10,000 mg/L. PHF solutions of 0.1, 1, 10 and 100 mg/L were sprayed on the top of a bread slice whereas 1,000 and 10,000 mg/L PHF solutions were deposited by pipette as drops having a volume of 0.3 mL on the bread slice. *A. niger* inoculum at a concentration of $1 \times 10^4$ to $2 \times 10^4$ CFU/mL was subsequently sprayed on the top side of the bread. The bread was placed in a sterile tray, inoculated side up, and the tray was sealed with plastic wrap. In like manner depositions were applied to peaches as given in Table 2. Control and PHF coated samples were stored in the dark at room temperature and 90% humidity. Bread and peaches were monitored and photographed on a daily basis.

TABLE 1

Details of bread experiment (1 "spray" contains 0.11 ± 0.01 mL of liquid)

|  | 0.1, 1, 10, 100 mg/L PHF | 1,000 and 10,000 mg/L PHF | Control |
|---|---|---|---|
| DI water | 5 sprays on each side | 10 sprays on each side | 15 sprays on each side |
| PHF solution | 10 sprays on top | Pipette 0.3 mL on top | |
| *Aspergillus niger* | | 1 spray on top | |

TABLE 2

Details of peach experiment

|  | 0.1, 1, 10, 100 mg/L PHF | 1,000 and 10,000 mg/L PHF | Control |
|---|---|---|---|
| DI water | 5 sprays on surface | 10 sprays on surface | 15 sprays on surface |
| PHF solution | 10 sprays on surface | Pipette 0.3 mL randomly on surface | |
| *Aspergillus niger* | | 2 sprays on surface | |

Data Analysis

All experiments were run in triplicate or larger, and data is presented as the mean±the standard deviation (SD). Statistical analyses were performed using one-way analysis of variance (ANOVA) followed by Dunnett's test with an NCSS program (2004). A p value of less than 0.05 is considered to be statistically significant.

EXAMPLE 1

Growth of *P. subcapitata*

Figure 2:
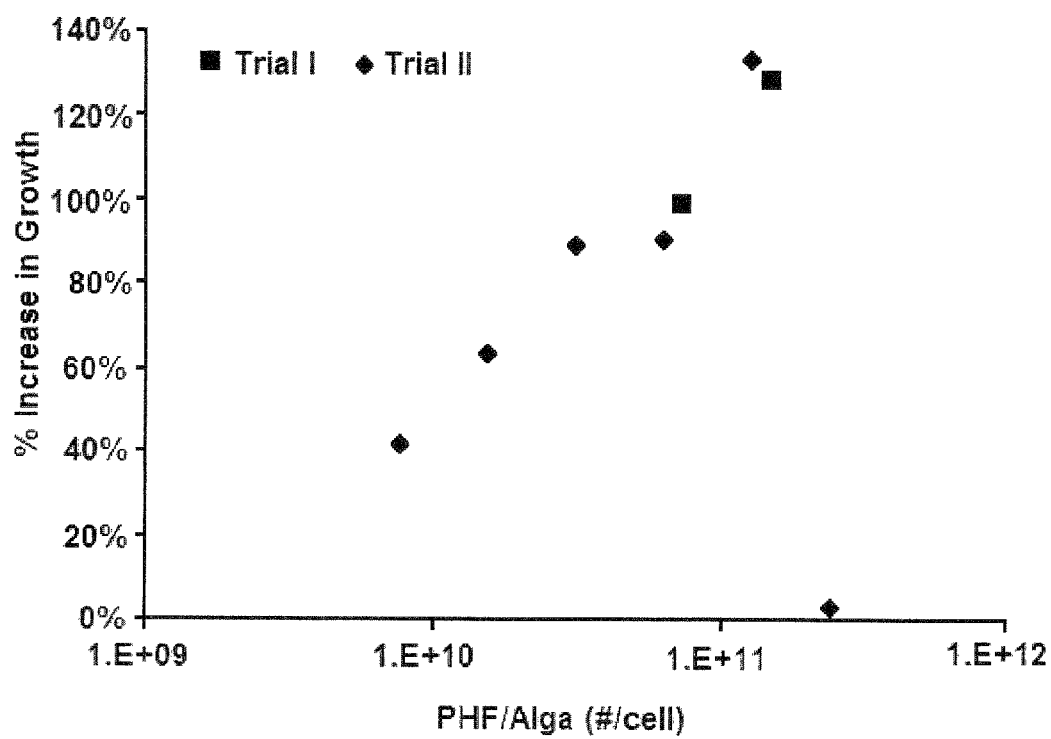
FIG. 2 shows a graph for the % increase in growth of *P. subcapitata* for various quantities of PHF per algae cell using a hemocytometer (Trial I) and by an absorbance measurement (Trial II) according to an embodiment of the invention.

Preliminary determination of algae growth using a hemocytometer in a first trial and in a second trial by absorbance measurements indicated that upon introduction of an effective quantity of PHF per cell of algae of about $1 \times 10^{10}$ to about $3 \times 10^{11}$ significant growth could be stimulated as shown in FIG. 2.

Figure 3:
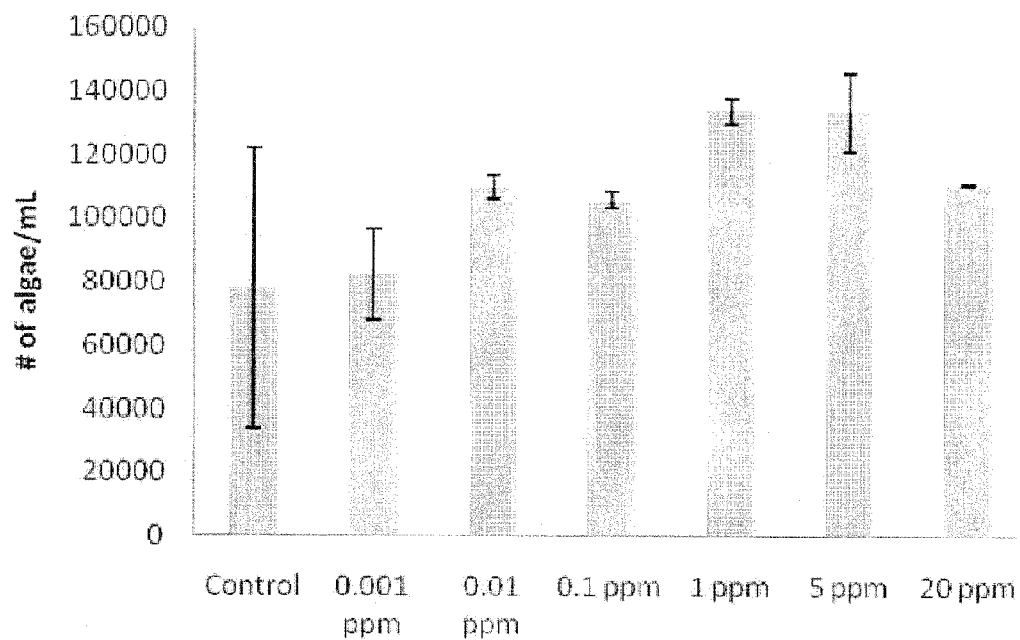
FIG. 3 shows a bar graph of the number of *P. subcapitata* cells per mL in a preliminary algal assay procedure (PAAP) culture medium for a control and various PHF treated samples after 4 days according to an embodiment of the invention.

For subsequent studies using cell number count between 3.4 and 8 μm using a Coulter Multisizer III to determine the average concentration of *P. subcapitata*, values for each treatment are indicated in FIG. 3. PHF exposures at 1 mg/L and 5 mg/L significantly increased the growth of algae by 72% compared to the control treatment. Other PHF concentrations did not display a significant effect at $\alpha=0.05$, although elevated mean values were observed over the control.

EXAMPLE 2

Survival of *C. dubia*

Exposure to PHF concentrations of 0 to 20 mg/L over a period of 7 days did not kill *C. dubia* (Table 3), indicating no acute (48-hour) or chronic (7-day) mortality.

TABLE 3

Survival of *Daphnia* within 7 days

| PHF concentration (mg/L) | # of exposed daphnids | # of survival after 48 hours | # of survival after 7 days |
|---|---|---|---|
| 0 | 5 | 5 | 5 |
| 0.001 | 5 | 5 | 5 |
| 0.01 | 5 | 5 | 4.5 ± 0.5 |
| 0.1 | 5 | 5 | 5 |
| 1 | 5 | 5 | 5 |
| 5 | 5 | 5 | 5 |
| 20 | 5 | 5 | 5 |

EXAMPLE 3

Reproductive Effect of PHFs on *C. dubia*

Figure 4:
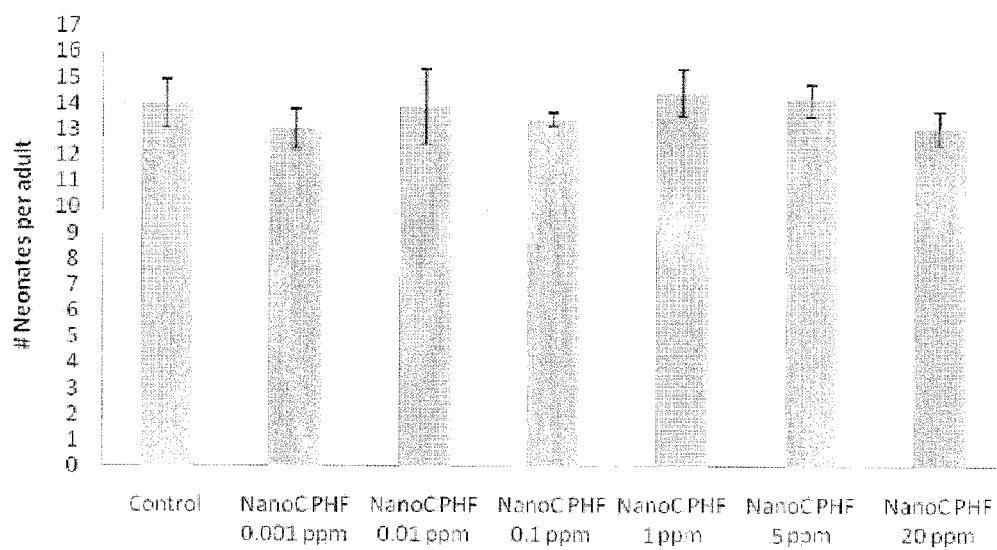
FIG. 4 shows a bar graph of 7-day *Daphnia* reproduction (neonates per adult) in control and various PHF treated samples according to an embodiment of the invention.

The average number of *Daphnia* offspring produced in the first 7 days was not significantly affected by PHF at all tested concentrations relative to controls (FIG. 4). Similarly, the average number of neonates produced in each PHF treatment over the lifetime of the tested daphnids were not significantly different from control (Table 4).

TABLE 4

Total *Daphnia* reproduction over lifetime

| PHF Concentration (mg/L) | # of Neonates (Mean ± SD) | % Difference from Control |
|---|---|---|
| 0 | 725 ± 313 | |
| 0.001 | 717 ± 103 | −1.00 |
| 0.01 | 715 ± 255 | −1.38 |
| 0.1 | 460 ± 208 | −36.54 |
| 1 | 855 ± 80 | 17.98 |
| 5 | 779 ± 154 | 7.52 |
| 20 | 997 ± 60 | 37.65 |

EXAMPLE 4

Impacts of PHF on *Daphnia* Body Growth

Figure 5:
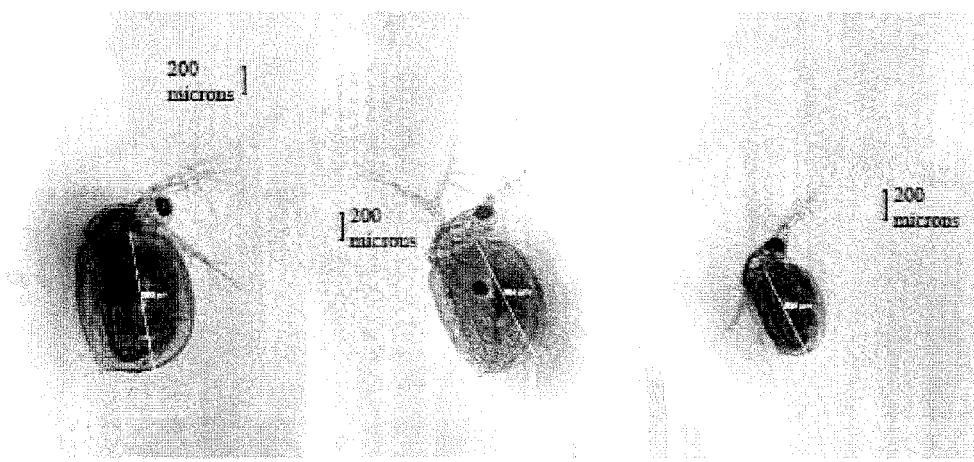
FIG. 5 shows microscopic images (10× magnification) of average sized daphnids exposed to a) no PHF (control), b) 0.001 mg/L of PHF, and c) 20 mg/L of PHF after 2 days according to an embodiment of the invention.
Figure 6:
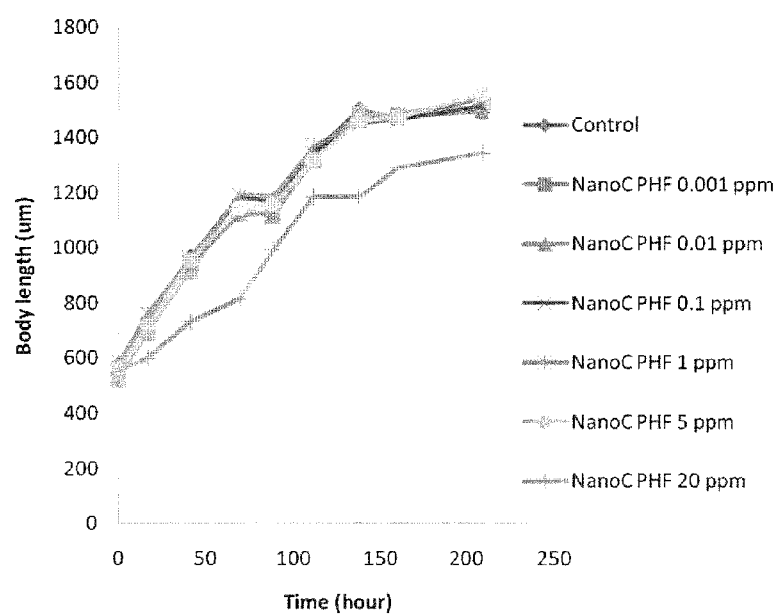
FIG. 6 shows a plot of the body lengths increase for daphnids over an 8 day period for a control population and populations with various PHF concentrations from 0.001 to 20 mg/L according to an embodiment of the invention.

FIG. 5 shows example micrographs taken for the daphnids in the control, 0.001 ppm and 20 mg/L of PHF treatments after 2-day exposure. Accumulation of PHF was clearly observed in the *Daphnia* gut under microscope observation and the gut color darkened with increasing PHF concentration. PHF showed no observable effects on the *Daphnia* growth at concentrations of 5 mg/L or lower (FIG. 6). At 20 mg/L of PHFs, growth appeared to slow although the growth inhibition may be due to continuous irradiation of the sample over the two days.

EXAMPLE 5

Effects of PHF on the Lifespan of *C. dubia*

Figure 7:
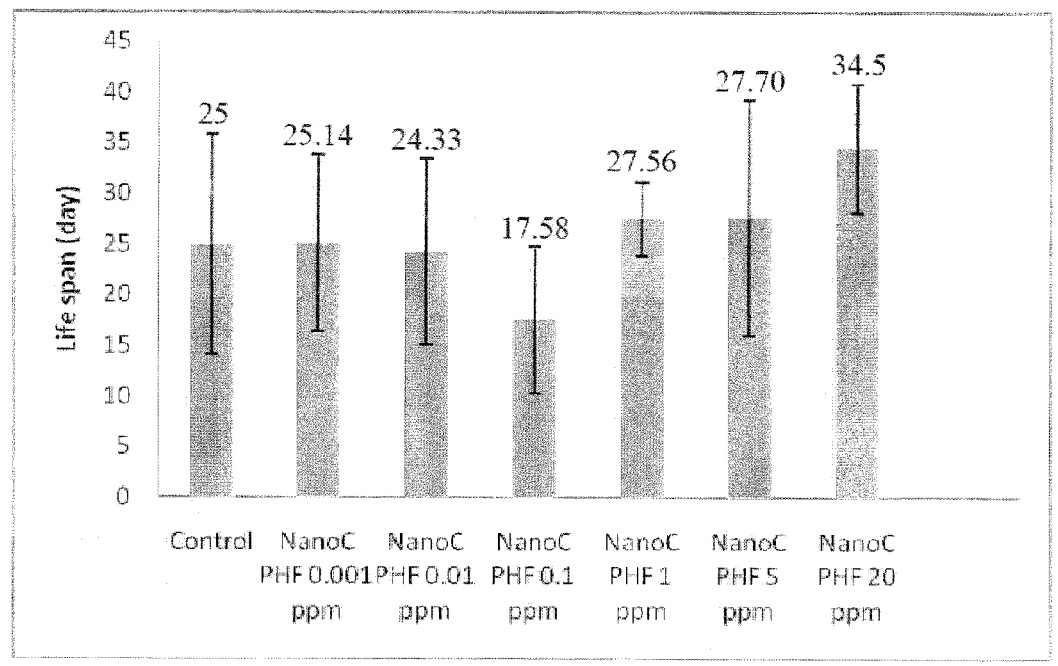
FIG. 7 shows a bar graph for the lifespan of daphnids for a control population and populations with various PHF concentrations from 0.001 to 20 mg/L according to an embodiment of the invention.

Daphnids used for reproduction study were kept throughout their lifetimes. At 20 mg/L of PHF, lifespan increased significantly (p<0.05), with a mean value approximately 38% more than the control (FIG. 7). In contrast, 0.1 mg/L appeared to have a significant inhibitory effect on the *Daphnia* lifespan, whereas other concentrations had no significant effect.

EXAMPLE 6

Growth of *Aspergillus niger*

Figure 8:
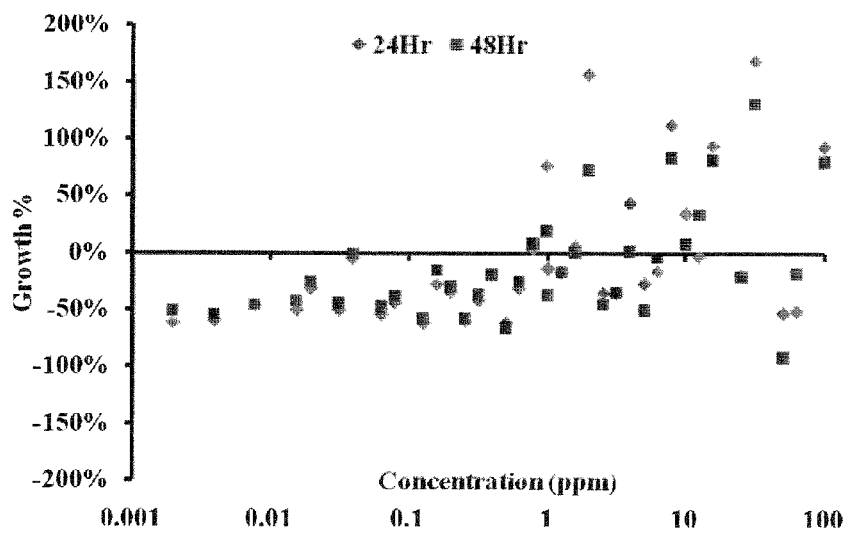
FIG. 8 shows the growth % of *Aspergillus niger* in the presence of PHFs using 96-well plate standard micro-dilution protocol (media: amended RPMI 1640) according to an embodiment of the invention.
Figure 9:
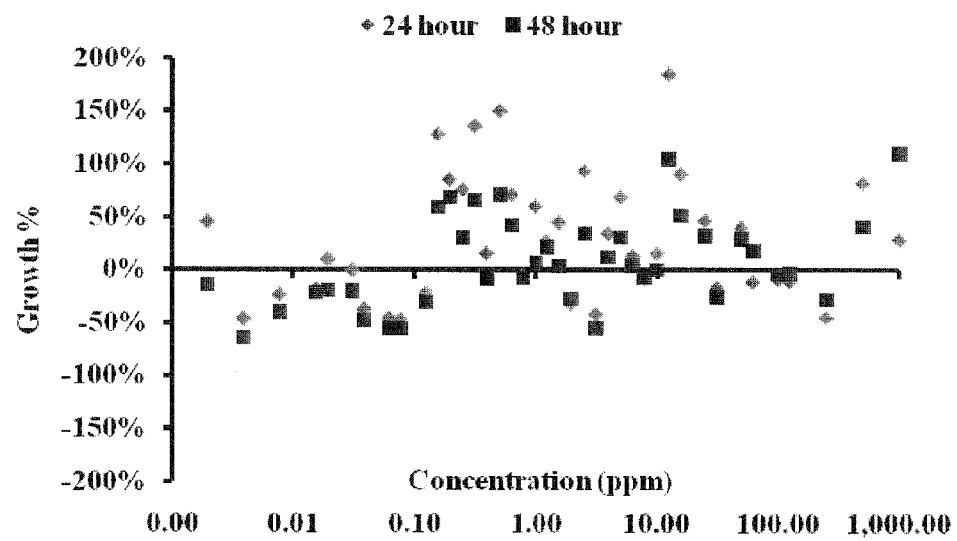
FIG. 9 shows the growth % of *Aspergillus niger* in the presence of PHFs using 96-well plate standard micro-dilution protocol (media: Potato dextrose broth) according to an embodiment of the invention.
Figure 10:
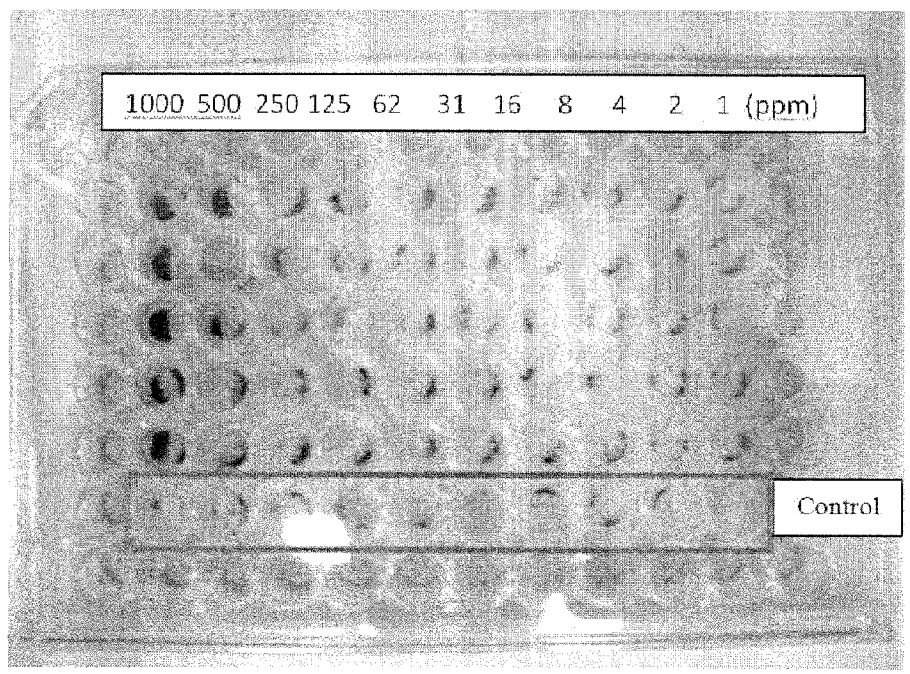
FIG. 10 shows a photographic reproduction of a 96-well plate test after 120-hour incubation where a column of test cells having *A. niger* exposed to 1,000 mg/L PHF shows significantly higher growth than control or other PHF quantities according to an embodiment of the invention.

A 96-well plate standard micro-dilution protocol was conducted on *Aspergillus niger*. The growth %, calculated according to equation (1), is plotted in FIGS. 8 and 9 for *A. niger*. Positive value of growth % indicates stimulation of growth, while negative value is an indicator of inhibition. In FIG. 8 (media: amended RPMI 1640), the general trend of the scatter points indicates that PHF at lower concentration inhibits growth of *A. niger*, and as the concentration of PHF increases to more than 10 mg/L, stimulatory growth effect becomes quite significant. A similar trend was also observed in FIG. 9, in which the experiment was conducted in a different media (PDB). A photo, shown in FIG. 10, was taken after exposure of *A. niger* to PHF for 120 hours (media: amended RPMI 1640). In FIG. 10, the second column (with 1000 mg/L of PHF) has many more spores formed compared to those of control, indicating that PHF at higher concentration can stimulate the reproduction of *A. niger*.

Figure 11:
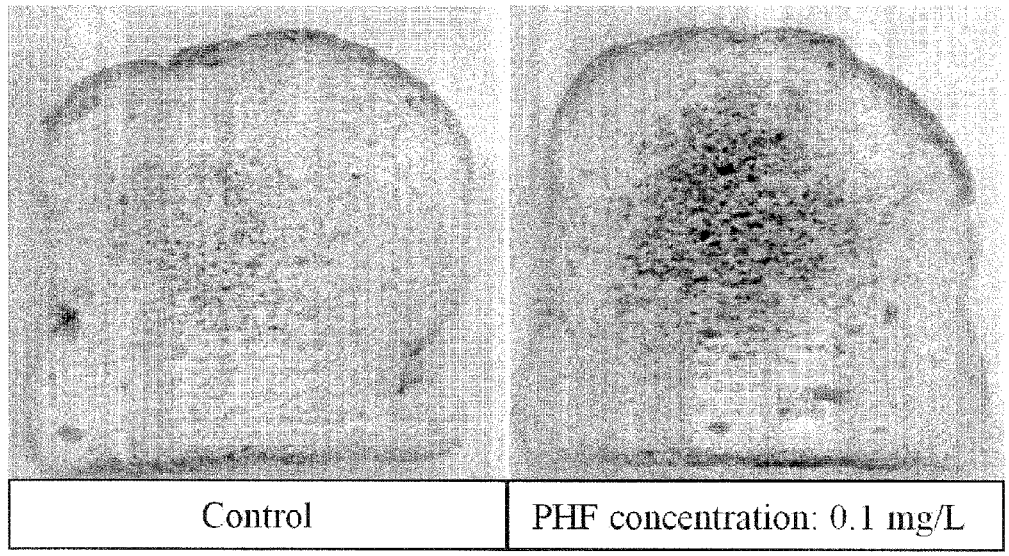
FIG. 11 shows the growth of *Aspergillus niger* on white bread coated with a 0.1 mg/L PHF solution and control bread after 3-day incubation at room temperature and 90% relative humidity according to an embodiment of the invention.

Further experiments were conducted on two edible substrates, bread and peaches. Pictures showing significant growth of *A. niger* are present in FIGS. 11, 12 and 13. In FIG. 11, bread coated with 0.1 mg/L of PHF solution showed increased growth of fungi on bread surface after 3 days of incubation.

Figure 12:
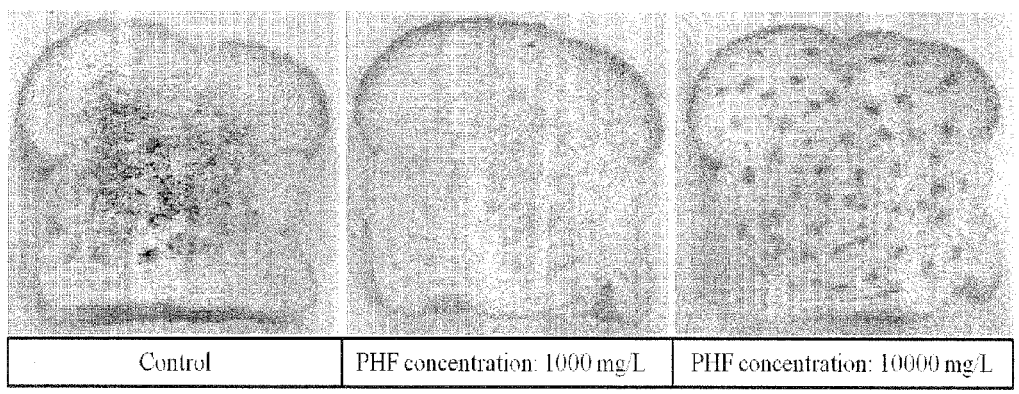
FIG. 12 shows the growth of *Aspergillus niger* on white bread coated with a 1000 and 10000 mg/L, PHF solution and control bread after 3-day incubation at room temperature and 90% relative humidity according to an embodiment of the invention.

Photographs with different concentrations of PHF exposed to *A. niger* are displayed in FIG. 12, which indicates that bread with high concentration (1000 and 10000 mg/L) of PHF exhibit a strong inhibitory effect on *A. niger*, as opposed to the bread coated with 0.1 mg/L PHF solution which showed the promotion of fungal growth on the bread surface.

Figure 13:
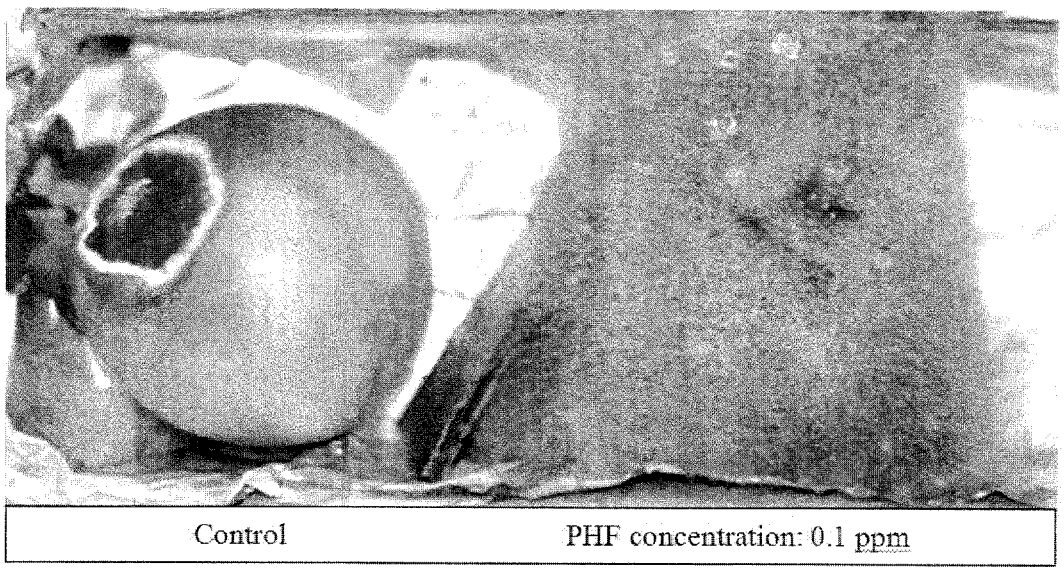
FIG. 13 shows the growth of *Aspergillus niger* on a peach coated with a 0.1 mg/L PHF solution (right) and a control peach (left) after an 8-day incubation at room temperature and 90% relative humidity according to an embodiment of the invention.

In case of peaches, substantial growth of fungi was observed after 8 days of incubation for peach coated with 0.1 mg/L PHF solution, as shown in FIG. 13. Higher concentrations of PHF resulted in inhibition of fungal growth on peaches.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of increasing biomass and/or rate of reproduction of an in vitro culture of Psuedokirchneriella subcapitata that is not in a diseased, infected, or toxic state with a solution comprising contacting the culture with a concentration of 1 mg/L to 5 mg/L of polyhydroxylated fullerenes (PHFs).

2. A method of increasing biomass and/or rate of reproduction of an in vitro culture of *Ceriodaphnia dubia* that is not in a diseased, infected, or toxic state with a solution comprising contacting the culture with a concentration that is greater than or equal to 20 mg/L of polyhydroxylated fullerenes (PHFs).

3. A method of increasing biomass and/or rate of reproduction of an in vitro culture of *Aspergillus niger* that is not in a diseased, infected, or toxic state with a solution comprising contacting the culture with a concentration that is greater than or equal to 10 mg/L of polyhydroxylated fullerenes (PHFs).

* * * * *